United States Patent
Jin et al.

(10) Patent No.: US 6,805,879 B2
(45) Date of Patent: Oct. 19, 2004

(54) STABLE POLYMER AQUEOUS/AQUEOUS EMULSION SYSTEM AND USES THEREOF

(75) Inventors: Tuo Jin, Highland Park, NJ (US); Li Chen, Toronto (CA); Hua Zhu, Plainsboro, NJ (US)

(73) Assignee: BioPharm Solutions Inc., Highland Park, NJ (US)

( * ) Notice: Subject to any disclaimer, the term of this patent is extended or adjusted under 35 U.S.C. 154(b) by 0 days.

(21) Appl. No.: 09/886,555

(22) Filed: Jun. 21, 2001

(65) Prior Publication Data

US 2002/0055461 A1 May 9, 2002

Related U.S. Application Data

(60) Provisional application No. 60/214,037, filed on Jun. 23, 2000.

(51) Int. Cl.$^7$ ............................................. A61K 9/127
(52) U.S. Cl. ..................... 424/450; 424/489; 424/490; 424/496; 424/497
(58) Field of Search ................ 424/450, 489, 424/490, 496, 497

(56) References Cited

U.S. PATENT DOCUMENTS 6,303,148 B1 * 10/2001 Hennink et al.

FOREIGN PATENT DOCUMENTS

| WO | 9822093 | 5/1993 |
| WO | 9800170 | 1/1998 |

OTHER PUBLICATIONS

"Biodegradable dextran microspheres for controlled release of pharmaceutical proteins," OctoPlus, Mar. 21–24, 2000 [Exhibit 3].

P. Langer and J. Folkman, "Polymers for the sustained release of proteins and other macromolecules;" Nature, 263, 797–800 (1976) [Exhibit 4].

S. Cohen and H. Berstein, Microparticutate Systems for the Delivery of Proteins and Vaccines; Marcel Dekker, New York, 1996 [Exhibit 5].

R. Bodmeier, H. Chen, P. Tyle and P. Jarosz, "Pseudophedrine HC1 microspheres formulated into an oral suspension dosage form;" J. Controlled Bol., 15, 65–77 (1991) [Exhibit 6].

M.J. Alonso, R.K. Gupta, C. Min, G.R. Siber and R. Langer, "Biodegradable microspheres as controlled–release tetanus toxoid delivery systems;" Vaccine, 12, 299 (1994) [Exhibit 7].

R.J. Henry and C.P. Szustkiewicz, "The preparation of Protein–Free Filtrates," in Clinical Chemistry, Principals and Technics; R. J. Henry, edit; Press: Harper & Row, 1964 [Exhibit 8].

* cited by examiner

Primary Examiner—Leon B. Lankford, Jr.
(74) Attorney, Agent, or Firm—Albert Wai-Kit Chan; Mark Elkins

(57) ABSTRACT

This invention provides a stable aqueous/aqueous emulsion system which is prepared with a hydrophilic polymer. This invention also provides the method of preparing a stable aqueous/aqueous emulsion. Finally, this invention provides an encapsulation comprising the emulsion system which is prepared with a hydrophilic polymer.

9 Claims, 7 Drawing Sheets

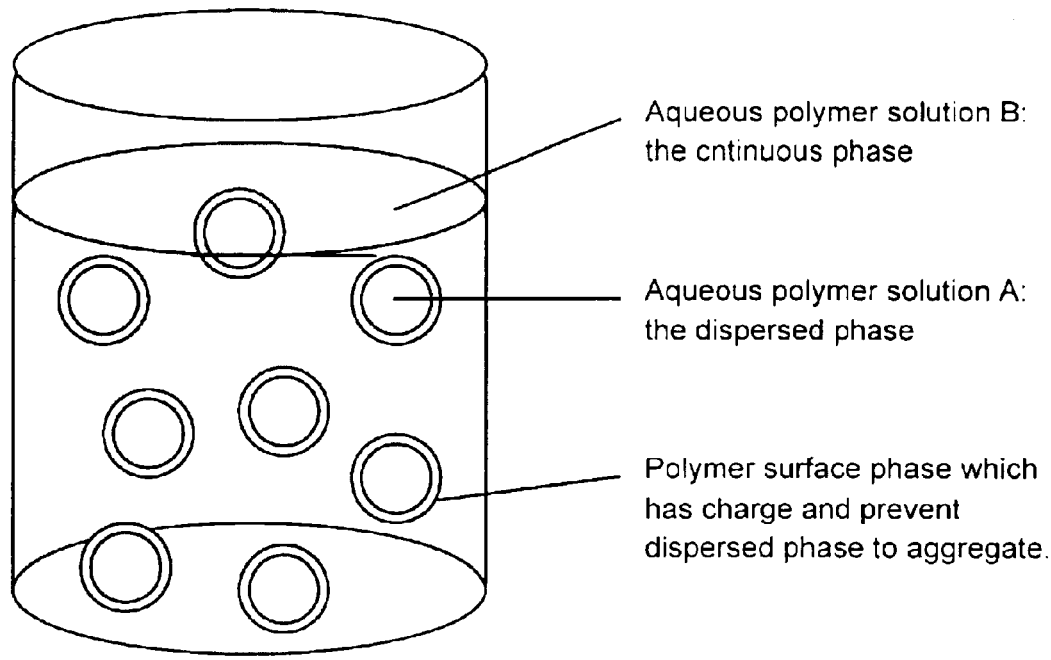

Figure 1. Polymer aqueous/aqueous emulsion system.

Polymer solution A and polymer solution B are immiscible, thus A can be dispersed into B under a shear stress. The third polymer carries charge and is fairly immiscible with both A and B at low concentration, so that it tends to be rich at the interface of A and B, and forms a charged surface. The charged surface effectively prevent aggregation and fusion of the dispersed phase (See *Example 1* in the paragraph). Therapeutic agents such as proteins, liposomes and viruses are partitioned and encapsulated in the dispersed phase and subjected to lyophlization (See *Examples 2, 3 and 4*).

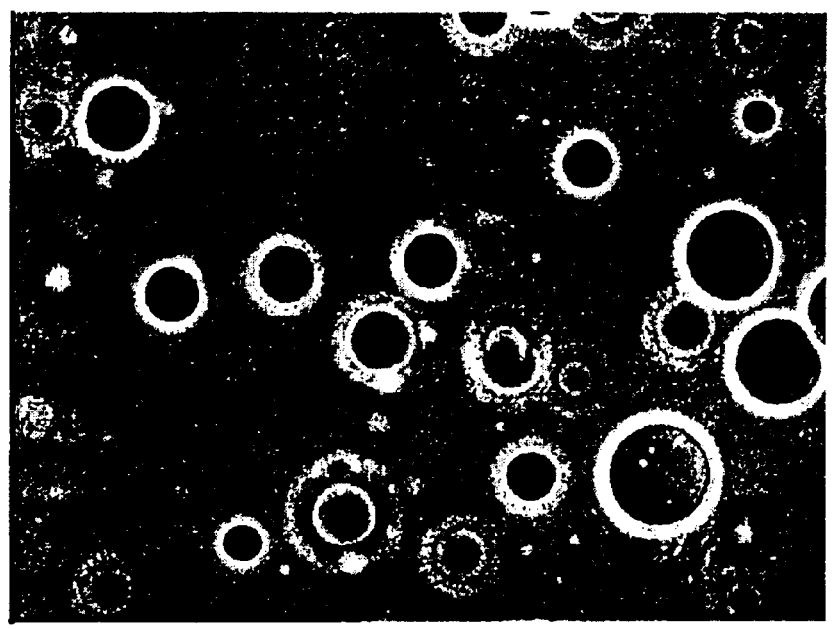
Figure 2. Microscopic image of polymer aqueous/aqueous emulsion

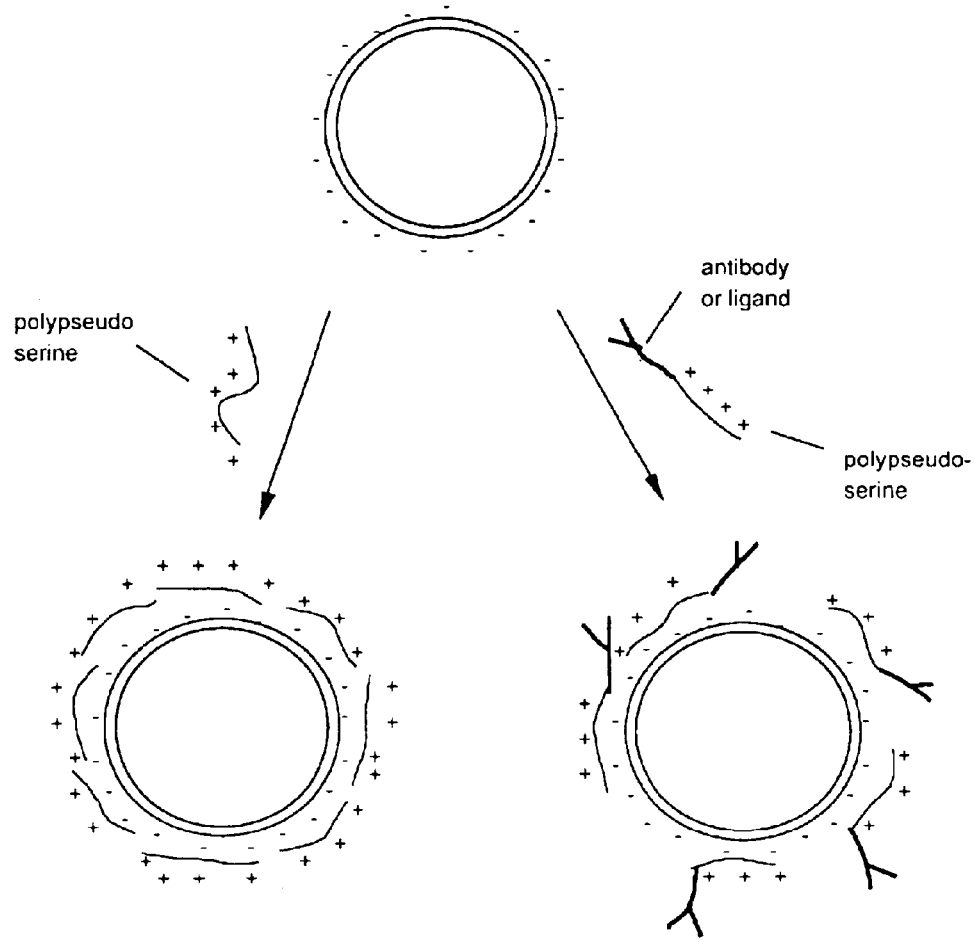

Figure 3. Secondary surface modification of polymer aqueous droplets dispersed in a polymer aqueous continuous phase.

The surface of the dispersed phase in Figure 1 can be further modified for functionization (See *Additional applications* in the paragraph). Permeability barrier can be assembled on the surface by ionic cross-linking with a degradable polymer having opposite charge, or by assembly of a lipid bilayer having opposite charge. Release rate of encapsulated therapeutics can be adjusted by selecting the cross-linking polymer in terms of chain length and structure of desired degradation rate (polyaminoacid or polypeptide for example). Targeting moeieties (antibodies or ligands) can be immobilized on the surface through ionic interaction or hydrophobic interaction (in the case of lipid bilayer assembly).

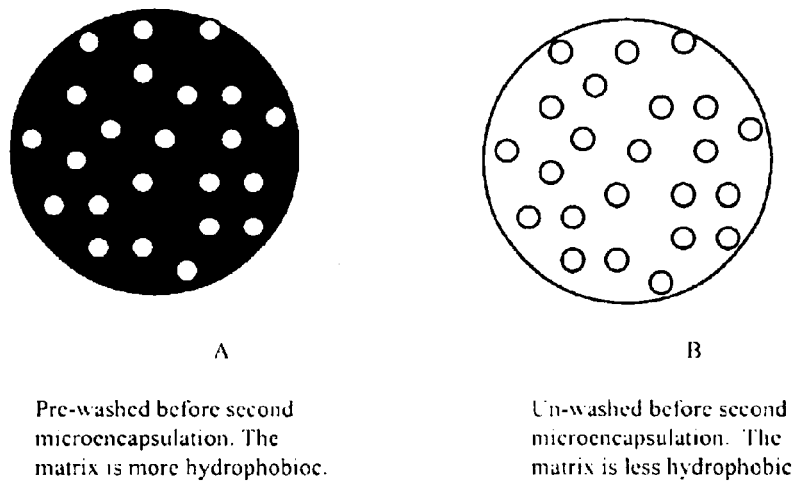

A

Pre-washed before second microencapsulation. The matrix is more hydrophobioc.

B

Un-washed before second microencapsulation. The matrix is less hydrophobic.

Figure 4. Microspheres prepared by double-microencapsulation through solid-in-oil-in-water emulsification The powder formed by drying of the aqueous/aqueous emulsion can be further encapsulated into hydrophobic, degradable polymer microspheres. Since methane dichloride, a commonly used solvent in polymer microsphere preparation, dissolves reactant B (the continuous phase of the A/A emulsion) but does not interact with reactant A (the dispersed phase), reactant B can be removed from the lyophilized powder simply by washing with the solvent. Microspheres which encapsulate the lyophilized powder possess more hydrophobic matrix if reactant B is washed out, but less hydrophobic if reactant B remains. This structural difference can affect degradation rate of the polymer matrix and diffusion rate through the polymer matrix, thus the release profile of offers encapsulated therapeutics can be adjusted by the content of reactant B remained.

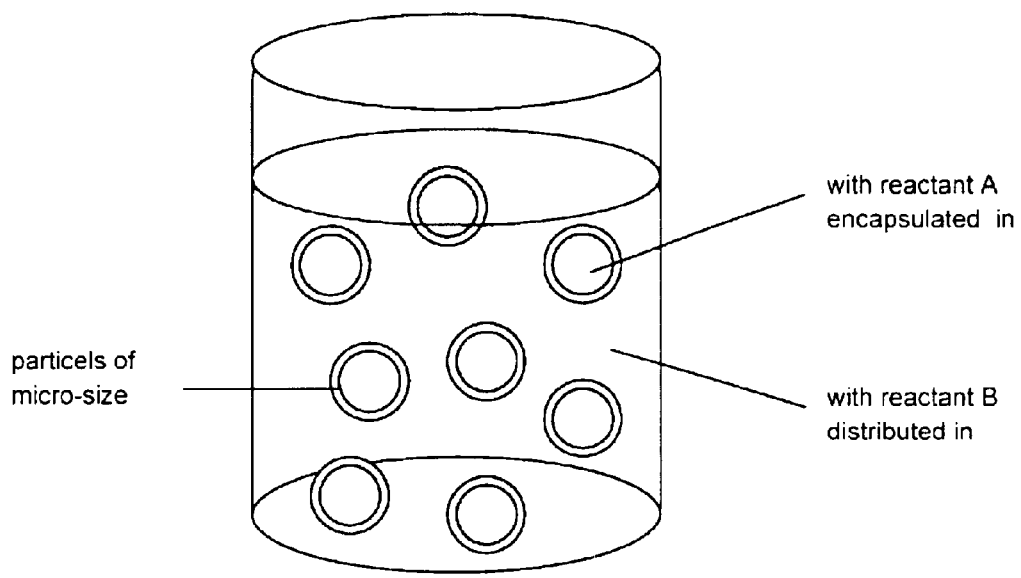

Figure 5. Nano-sized preparation using polymer aqueous/aqueous emulsion.

Nano-meter-sized crystals and other assemblies formed from two reactants can be prepared using the emulsion system (See reference [14]). Reactant A is usually those which partitioned and encapsulated into the dispersed phase. Reactant B is those which are distributed to both phases. Since A is isolated with limited quantity in each micro-sized droplet, when the assembly process proceeds, the limited accessibility of the reactants ensures a small sized product. Nano-sized preparation is useful in produce of both therapeutic and diagnostic agents.

Figure 6. Microscopic image of reconstituted AmB/liposomes (of SUV) which were freeze-dried after loading into the polymer emulsion. (The bright particle is a reffence for focusing.)

Liposomes are not visible due to size, indicating that the small unilamellar structure is protected by the polymer emulsion system.

Figure 7. Microscopic image of reconstituted AmB/SUV which were freeze-dried without loading into the polymer emulsion.

Liposome particles are observed after reconstitution (re-hydration) of the small unilamellar liposomes after lyophilization without protection by the polymer emulsion system.

STABLE POLYMER AQUEOUS/AQUEOUS EMULSION SYSTEM AND USES THEREOF

This application claims benefit of U.S. Pat. application Ser. No. 60/214,037, filed on Jun. 23, 2000, the content of which is incorporated here into this application.

Throughout this application, various references are referred to. Disclosures of these publications in their entireties are hereby incorporated by reference into this application to more fully describe the state of the art to which this invention pertains.

BACKGROUND OF THE INVENTION

While more and more biological therapeutic agents have become available due to the advances in molecular biology, immunology and microbiology, pharmaceutical development (e.g. development of appropriate dosage forms) for delivery of these proteins is behind the state of art of biotechnology. The situation is attributed to the difficulties in formulating these agents which are less permeable to tissue membranes, highly degradable at the sites of administration and therapy, short shelf life, and structurally susceptible during conventional formulation processes. To develop commercially available and patient compliant dosage forms for these therapeutics, the above-mentioned issues must be addressed respectively.

The disclosed are a novel material system named polymer aqueous/aqueous emulsions and its pharmaceutical and biotechnological applications. To meet desired therapeutic purposes such as sustained release, targeting to therapeutic sites, extension of bio-activity, and reducing toxicity, many chemical and biological therapeutics need to be microencapsulated[1,2]. Emulsification is a key step in microencapsulation during which active ingredients are incorporated into the dispersed phase. Conventional emulsions are made by dispersing a hydrophilic phase (dispersed phase) into a hydrophobic phase (continuous phase) or vice versa (W/O or O/W)[3]. For microencapsulation of protein therapeutics, a double emulsification process, called water-in-oil-in-water (W/O/W) emulsification, is used. The protein solution is first dispersed into a polymer solution dissolved in an organic solvent, and the resulted emulsion is further dispersed into a dilute aqueous solution of another polymer, followed by solvent evaporation or extraction. The major problem associated with the conventional microencapsulation procedures is that the protein molecules may be denaturated by contacting with the organic solvents which are indispensable in the processes. Although surfactants and/or hydrogel solutions are used in the first emulsification to protect the proteins[4,5], they are only effective to certain relatively stable proteins. A microencapsulation process which is free of organic solvents is highly demanded.

For aqueous systems, particles may be formed through various precipitation mechanisms such as salting out[6], acid-base interaction[7], pH assistant precipitation. For these mechanisms, concentrated salts, extreme pH or protein (ionic) cross-link agents are unavoidable. These are all considered chemical hazards to the activity of biological therapeutics.

Two polymer aqueous solutions may be immicsible due to their chain length and structural difference[8]. Such polymer aqueous two-phase systems (which are not emulsions but block phases) are practically used for protein purification[8,9]. Their aqueous nature and relatively low interfacial tension provide excellent compatibility with soluble proteins in terms of preventing protein conformation change. Protein purification is based on their partition which favors one of the aqueous polymer phase with impurities partitioning into the other. The practice of protein purification is evident that proteins can be distributed into one of the aqueous phases with biological activity intact. This two-phase system readily forms two block phases after mixing. For microencapsulation purpose, however, a stable emulsion must be formed with the two polymer aqueous solutions.

This invention is aimed to address the above-mentioned issues and to develop a new formulation strategy for susceptible therapeutics especially biological agents.

SUMMARY OF THE INVENTION

The present invention provides a stable aqueous/aqueous emulsion system which is prepared with a hydrophilic polymer.

This invention also provides the method of preparing a stable aqueous/aqueous emulsion comprising steps of: a) selecting appropriate polymeric materials for dispersed phase and continuous phase which are immiscible, biocompatible and have biased partition to the active ingredients to be encapsulated; b) selecting appropriate surface modifiers which are charged, non-toxic, and possessing a moderate interfacial tension between the above two phases; c) developing phase diagram for the above; and d) dispersing the dispersed phase into the continuous phase under an appropriate shear stress.

Finally, the invention provides an encapsulation comprising the emulsion system which is prepared with a hydrophilic polymer.

The present invention demonstrates a stable emulsion system which provides the solution for all the problems raised above by that both the dispersed and the continuous phases are formed from aqueous solutions without concentrated salts, extreme pH, and other chemical hazards.

Water soluble proteins, liposomes, live viruses and other therapeutic agents can be microencapsulated on the bases of their partition favoring the dispersed phase, and released or reconstituted upon or prior to administration with their original morphology and activity preserved.

The emulsion can be dried to fine powder through freeze-drying, spray drying and other methods, and subjected to further treatment: coating, double-microencapsulation, compressing and other procedures by which a variety of pharmaceutical dosage forms including controlled release systems and targeted delivery systems can be prepared.

For biological agents including live viruses, encapsulation into the dry form can not only improve their stability and shelf-life, but also avoid expensive cold-chain (−20° C.) in transportation and application. This is important for many developing countries where cold-chain is not available.

All the polymer materials used in the invented emulsion system (including dispersed phase, the continuous phase and the surface stabilizing agent) are biocompatible and good for internal use on humans.

DETAILED DESCRIPTION OF THE FIGURES

FIG. 1. Polymer aqueous/aqueous emulsion system.

Polymer solution A and polymer solution B are immiscible, thus A can be dispersed into B under a shear stress. The third polymer carries charge and is fairly immiscible with both A and B at low concentration, so that it tends to be rich at the interface of A and B, and forms a charged surface. The charged surface effectively prevents aggregation and fusion of the dispersed phase (See Example 1 in the paragraph). Therapeutic agents such as proteins, liposomes and viruses are partitioned and encapsulated in the dispersed phase and subjected to lyophlization (See Examples 2, 3 and 4).

FIG. 2. Microscopic image of polymer aqueous/aqueous emulsion.

FIG. 3. Secondary surface modification of polymer aqueous droplets dispersed in a polymer aqueous continuous phase.

The surface of the dispersed phase in FIG. 1 can be further modified for functionization (See Additional applications in the paragraph). Permeability barrier can be assembled on the surface by ionic cross-linking with a degradable polymer having opposite charge, or by assembly of a lipid bilayer having opposite charge. Release rate of encapsulated therapeutics can be adjusted by selecting the cross-linking polymer in terms of chain length and structure of desired degradation rate (polyaminoacid or polypeptide for example). Targeting moeieties (antibodies or ligands) can be immobilized on the surface through ionic interaction or hydrophobic interaction (in the case of lipid bilayer assembly).

FIG. 4. Microspheres prepared by double-microencapsulation through solid-in-oil-in-water emulsification.

The powder formed by drying of the aqueous/aqueous emulsion can be further encapsulated into hydrophobic, degradable polymer microspheres. Since methane dichloride, a commonly used solvent in polymer microsphere preparation, dissolves phase B (the continuous phase of the A/A emulsion) but does not interact with phase A (the dispersed phase), the phase B can be removed from the lyophilized powder simply by washing with the solvent. Microspheres which encapsulate the lyophilized powder possess more hydrophobic matrix if the phase B is washed out, but less hydrophobic if the phase B remains. This structural difference can affect degradation rate of the polymer matrix and diffusion rate through the polymer matrix, thus the release profile of encapsulated therapeutics can be adjusted by the content of the phase B remained.

FIG. 5. Nano-sized preparation using polymer aqueous/aqueous emulsion.

Nano-meter-sized crystals and other assemblies formed from two reactants can be prepared using the emulsion system (See reference [14]). Reactant A is usually those which partitioned and encapsulated into the dispersed phase. Reactant B is those which are distributed to both phases. Since A is isolated with limited quantity in each micro-sized droplet, when the assembly process proceeds, the limited accessibility of the reactants ensures a small sized product. Nano-sized preparation is useful in produce of both therapeutic and diagnostic agents.

FIG. 6. Microscopic image of reconstituted AmB/liposomes (of SUV) which were freeze-dried after loading into the polymer emulsion.

Liposomes encapsulated into the polymer emulsion system, followed by lyophilization, are not visible after reconstitution, indicating that their small unilamellar structure is protected by the polymer emulsion system.

FIG. 7. Microscopic image of reconstituted AmB/SUV which were freeze-dried without loading into the polymer emulsion.

Small liposomes (SUV) after direct lyophilization shows large particles when reconstituted, indicating aggregation and fusion of unprotected liposomes during the drying process

DETAILED DESCRIPTION OF THE INVENTION

The present invention provides a stable aqueous/aqueous emulsion system which is prepared with a hydrophilic polymer. This invention also provides the method of preparing a stable aqueous/aqueous emulsion comprising steps of: a) selecting appropriate polymeric materials for dispersed phase and continuous phase which are immiscible, biocompatible and have biased partition to the active ingredients to be encapsulated; b) selecting appropriate surface modifiers which are charged, non-toxic, and possessing a moderate interfacial tension between the above two phases; c) developing phase diagram for the above; and d) dispersing the dispersed phase into the continuous phase under an appropriate shear stress. This invention further provides the above aqueous/aqueous emulsion system with polymeric surface modifier.

In addition, this invention provides a method for encapsulating protein or peptide comprising the above emulsion system. In an embodiment, the encapsulated protein or peptide is used for sustained release formulations or dry powder formulations.

This invention further provides an encapsulation comprising the emulsion system which is prepared with a hydrophilic polymer. In an embodiment, the encapsulation encapsulates protein, peptide, virus, bacterium, or cell.

This invention also provides a liposome-based drug formulation which comprises the above emulsion system. Still further, the invention provides viral, bacterial or cell microencapsulation comprising the above emulsion system.

This invention also provides the nano-sized preparation comprising the above emulsion system. In an embodiment, the preparation is nano-sized crystallization, nano-sized precipitation or other nano-sized assembly.

Finally, this invention provides a diagnosis kit comprising the above emulsion system.

The polymer aqueous/aqueous emulsion system described in this invention is fundamentally different from existing emulsions which are prepared by dispersing a hydrophilic phases into a hydrophobic phase or the vice versa. This difference is extended to the so-called water-in-oil-in-water (W/O/W) emulsions. In any of these conventional emulsions, phase separation occurs between an aqueous phase and a water-immiscible organic phase. In the case of the present invention, phase separation occurs between two aqueous phases.

The emulsification process is distinct from those precipitation processes from aqueous solutions which are based on salting out, acid-base interaction, and pH-assisted precipitation. In the invented emulsification process, such mechanisms which rely on application of concentrated salts and extreme pH are not involved. Instead, phase separation between two polymer aqueous phases is due to positive enthalpy of mixing, ($\Delta H_M$), and reduced entropy of mixing, ($\Delta S_M$), as polymer chain increased.

This system is also different from polymer aqueous two-phase system which is used in protein purification. In addition to phase separation, the dispersed droplets must be stabilized to prevent fusion. This is accomplished by introducing a third aqueous polymer which is charged and adsorbed at the interface between the two immiscible polymer phases. The surface charges brought by the third polymer effectively prevent aggregation and fusion of the droplets.

In the present invention, applications of the polymer aqueous/aqueous emulsion system in pharmaceutical formulation were examined by microencapsulation of three representative agents: liposomes, proteins and live viruses. The new emulsion system showed encouraging result for each type of the agents, indicating its usefulness in formulating susceptible therapeutic agents.

Liposomes are used for formulating pharmaceutical dosage forms for intravenous injection (IV)[10]. For IV administration, the liposomes must be prepared and maintained in the form of small unilamella vesicles (SUV). However, during shelf time, the SUV aggregate and fuse to form large particles. The emulsion system may effectively protect and preserve the SUV structure of liposomes by encapsulating them into the dispersed phase and lyophlizing to dry powder. In our study, the protected SUV structure was reconstituted simply by adding water to the lyophlized powder (see FIG. 6). As the control, un-encapsulated SUV liposomes were lyophlized and re-hydrated, and found that the original SUV morphology was lost and converted to large multilamella vesicles (see FIG. 7).

In developing sustained release dosage forms for proteins, preventing denaturation of the therapeutic proteins in the formulation processes is a key issue. Denaturation of proteins in formulation processes is mainly due to contact with organic solvents used and strong interfacial tension between the dispersed and the continuous phases. The present invention offers a formulation environment which is free of these chemical hazards found in conventional microencapsulation processes which are regarded as the cause of protein denaturation. As an example, a conformation-sensitive enzyme, (β-galactosidase, was encapsulated with the polymer aqueous/aqueous emulsification technology and compared its activity with that un-encapsulated (the positive control) and that encapsulated with the conventional W/O method (the negative control). The enzymatic activity of the protein after release was comparable with the positive control, while that formulated with the W/O method showed no activity. The result confirms our hypothesis that protein conformation can be preserved during this new microencapsulation process.

In addition to protection of proteins from contact with organic solvents, the present system offers more useful physical chemical mechanisms in controlling released rate and release profile of encapsulated protein therapeutics. For biodegradable polymeric drug delivery systems, release rate of encapsulated therapeutics depends on the rate of degradation (chemical reaction). However, manipulating the rate of a chemical reaction in vivo is difficult due to the restrictions in changing reaction conditions such as temperature. For the microspheres made by the solid-in-oil-in-water methods, since the phase B (PEG) can be co-dissolved with the hydrophobic polymer (such as PLGA), the nature of the polymer matrix such as hydrophilicity/hydrophobicity, swellability and the rate of hydrolysis, can be adjusted by the content of the phase B (PEG) in the hydrophobic matrix (see FIG. 4). Moreover, release of PEG can open channels for dissolution of the phase A (dextran), thus lead to a diffusional mechanism for protein release.

Applications of this new material system have been extended to formulation of live viruses. Live viruses are used in some human vaccines [11] and many veterinary vaccines. To maintain the viral activity in infecting cells, cold-chain (−20° C.) is required in transportation and application of viral vaccines and other viral products. With the present invention, the viral products may be prepared as dry powder without losing their activity, so that room temperature maintenance will be possible. In a preliminary experiment, cytomegalo viruses (CMV) were encapsulated with the aqueous/aqueous emulsion system, followed by lyophlization. The dried viruses were then reconstituted with buffer and incubated with human foreskin fiber blast cells. The infection activity of the encapsulated viruses was compared with fresh viruses (positive control) and viruses lyophlized without the emulsion system (negative control). Again, an unequivocal result was attained that the encapsulated viruses showed an activity comparable to the positive control while the negative control showed no infection.

Details of the Invention

EXAMPLE 1

Preparation of Polymer Aqueous/Aqueous Emulsion

Method 1

Dextran (MW 100,000 to 1,000,000) and sodium alginate (low or medium viscosity) were dissolved in water at the dextran concentration of 10 to 50 w/v % and dextran to alginate ratio of 10:1 to 30:1. This solution is named solution A. An aqueous solution, named solution B, containing polyethylene glycol (PEG, MW 1,000 to 12,000) was prepared with PEG concentration ranging from 10 to 40 w/v %. Solution A was added into solution B at the volume ratio from 1:0.7 to 1:5 under a shear stress (stirring or homogenizing). The particle size distribution, which may be measured using a particle sizer for appropriate range, ranged as a function of the shear stress applied. Stability of the emulsion system was examined by placing it at room temperature for several weeks. Fusion was not observed (See FIG. 1).

Method 2

Solution A was prepared with Dextran (MW 100,000 to 1,000,000) only at the concentration of 10 to 50 w/v %. Solution B containing PEG and alginate of the above-mentioned molecular weight was prepared. The concentration of PEG ranged from 10 to 40 w/v % and PEG to alginate ratio ranged from 10:1 to 30:1. Solution A was dispersed into solution B with the same procedure as above. Stable emulsions were prepared as method 1.

EXAMPLE 2

Encapsulation of Liposomes

Partitioning of Liposomes

Solution A, dextrin 30 w/v % and solution B, PEG 25 w/v % were prepared. Small unilamellar vesicle (SUV) liposomes were prepared by sonication of a phospholipid (DOPC with 2% fluorescent lipid) water suspension (lipid/water=5~10 mg/ml). Prior to sonication, the lipid-water suspension was sealed with nitrogen. The sonication was sustained, with an interval for each 2 min. until the milky suspension converted to a transparent liquid phase. The resulted liquid was examined using a microscope, and no visible liposomes were found. The liposome suspension was added into solution A and well mixed, so that solution A became colored (yellow). Then solution A with liposome suspension was added to same solution B of the same volume, followed by stirring for 10 min. After the emulsified solution (containing A and B) was allowed to settle for 10 min, the cloudy emulsion became two clear block phases. The dextran phase, which at the bottom, was yellow, while the PEG phase was colorless. This is evident that the liposomes are mainly distributed in the dextran phase.

Encapsulation and Lyophlization of Liposomes

Solution A and B, same as in Example 1, were prepared. Small liposomes (SUV) were prepared as above without fluorescent lipids. The liposomes were first dispersed in solution A, followed by further emulsification with solution B. The resulted emulsion was allowed to settle over night, and no precipitation was observed. The sample was then frozen and subjected to a lyophlizer with vacuum better than $10^{-2}$ torr for over night.

The resulted dry powder was reconstituted by readily dissolving in water. The solution was clear and no visible liposomes were found under a microscope (See FIG. 6). For comparison, the same liposomes suspension was lyophlized directly without dispersing into the polymer solutions. Adding water to the directly lyophlized powder resulted in a milky suspension, and large (visible) liposomes were identified under a microscope (See FIG. 7). This experiment indicates that aqueous emulsion system can effectively protect the SUV structure from collapse during lyophlization process. The liposome (SUV) suspension was also dispersed into a dextran solution (solution A in Example 3), followed by lyophlization. Instead of fine powder, a hard block was resulted from this procedure. Dissolving the block sample required vortex for approximately 5 min.

EXAMPLE 3

Activity of β-Galactosidase After Microencapsulation

Encapsulation of β-Galactosidase

Beta-galactosidase (1000 unit/ml), 2 μl, was added into 0.25 ml solution A (same as in example 1), and mixed with pipetting. The resulted solution was dispersed slowly into solution B (example 1) under stirring at room temperature. The volume ratio of solution A and B was 1:1.

Encapsulation efficiency of the protein in the dispersed phase (the dextran phase) was examined by enzymatic activity of the protein in hydrolysis of 0-nitrophenyl-beta-D-galactopyranoside. Prior to enzymatic activity test, the dispersed phase was separated from the continuous phase by centrifugation at 500 G for 2 minutes.

A solution containing 30 mM Mg, 50 mM sodium phosphate, and 10 mM o-nitrophenyl-beta-D-galactopyranoside (the substrate) was prepared for assay of the enzymatic activity. This reactant solution, 0.3 ml, was mixed with each 0.5 ml of the dextran and PEG phases separated as above, respectively. The two assay samples were then incubated at 37° C. for 30 minutes, followed by addition of 0.5 ml 1 M Na2CO3 into each of them to terminate the reaction. Since the product of the reaction shows yellow color, the samples were subjected to a photometer and absorption at 420 nm was recorded. The absorbance was 0.82 and 0.08 for the dextran phase and the PEG phase, respectively. This result indicates that encapsulation efficiency is approximately 90%.

Protection of Protein Activity

To examine the compatibility of this emulsification process with conformational sensitive proteins, the enzymatic activity of encapsulated β-galactosidase was compared with two references. One was a positive control that the β-galactosidase solution was added into the reactant solution directly. The other was a negative control that 2 μl of the enzyme solution was added to 0.25 ml solution A (prepared as in example 1), followed by dispersing into a mineral oil. The protein in the W/O emulsion was recovered by washing the oil away with acetone and re-dissolving the pellet. After adding the reactant solution and incubation as above, the absorbance recorded was 0.81 and 0.00 for the positive and the negative controls, respectively. The result is unequivocal that the enzymatic activity of β-galactosidase was preserved during the microencapsulation process with the aqueous/aqueous emulsification but destroyed with the conventional W/o processes.

EXAMPLE 4

Dry Formulation of Live Viruses

Microencapsulation of Cytomegalo Viruses

Microencapsulation of cytomegalo viruses (CMV) was carried out under a procedure similar to that for liposome in example 2. Solution A containing 25 w/v % dextran 500T, 2 w/v % sodium alginate (medium viscosity), 50 mM Tris and 100 mM sodium chloride, and solution B contains 25 w/v % PEG 8000 were prepared for microencapsulation. CMV suspension, 5 μl in arbitrary unit was mixed with 0.4 ml of solution A, and then dispersed into 0.3 ml of solution B under magnetic stirring. While the initial volume of solution A was larger than that of solution B, the former still formed the dispersed phase. The emulsified samples were subjected to lyophlization as for liposomes in example 2 to form dry powders.

Infection Activity

The assay viral activity in infecting cells, four samples were prepared:

1) CMV in TN buffer (50 mM Tris, 100 mM NaCl), without lyophlization; (+ control)

2) CMV in TN buffer, lyophlized; (− control)

3) CMV microencapsulated but without lyophlization;

4) CMV microencapsulated and lyophlized;

After lyophlization, sample 2 and 4 were placed at room temperature for a day, and reconstituted by adding more TN buffer which dissolved the polymer powder. Then the four samples were incubated with human foreskin fiber blast cells. Each of the sample was diluted to six concentration (ten times different between two adjacent concentrations) and added to six dishes of the cells, respectively. The infections were monitored by formation of patches of the linear cells on the dishes. After incubation for a week, microencapsulated viruses (sample 3 and 4) showed comparable activity in infecting cells, but the activity was lower than that of the positive control (sample 1). The negative control (sample 2), however, showed no infection on any of the six dishes. The result is evident that the microencapsulation approach can protect viruses during lyophlization and lead to an active dry powder viral formulation.

Additional Applications

Controlled Release and Targeted Delivery of Therapeutics

The charged surface of the dispersed droplets can be further modified through ions cross-linking with a polymer of opposite charge (FIG. 2). Such charged polymers which are degradable and biocompatible are available (polypeptides, polyamonoacids [5], and chitosan, for example). By selecting the cross-linking agents (in terms of degradation rate and dissolution rate), release rate of encapsulated therapeutic agents can be adjusted.

The surface charge can be used to immobilize targeting moieties on the surface for cell-targeted delivery of therapeutics. Ligands or antibodies can be co-polymerized with a charged polyaminoacid [5], and immobilized on the particle surface (See FIG. 2).

The surface charge can also be used to assembly a phospholipid bilayer which enclosed the particle[12,13]. A supported phospholipid bilayer provides bio-function and cell surface environment to an artificial surface[14] which allows functional membrane proteins be immobilized and reconstituted on the surface.

Nano-Sized Preparation

Nano-meter-sized crystals and other solid particles are actively used in therapeutic (nano-cochleates [14]) and diagnostic (colloidal gold) agents. With the aqueous/aqueous emulsion system, one of reactants may be isolated into the micro-droplets waiting for the other reactant, which may be ions or other precipitation/crystallization agents, to diffuse into the droplet and initiate the reaction. Because one of the reactant in isolated in the micro-sized droplets, the growth of the crystal or other assembly is limited due to the limited accessibility between the reactant molecules.

REFERENCES

1. R. Langer and J. Folkman, "Polymers for the sustained release of proteins and other macromolecules"; *Nature*, 263, 797–800 (1976)
2. S. Cohen and H. Berstein, *Microparticulate systems for delivery of Proteis and vaccines;* Marcel Deker, New York, 1996
3. R. Bodmeier, H. Chen, P. Tyle and P. Jarosz, "Pseudo phedrine Hcl microspheres formulated into an oral suspension dosage form"; *J. controlled Rel.,* 15, 65–77 (1991)
4. M. J. Alonso, R. K. Gupta, C. Min, G. R. Siber and R. Langer, "Biodegradable microspheres as controlled release tetanus toxoid delivery systems"; *Vaccine,* 12, 299 (1994)
5. T. Jin and K. Solkoll, un-published data
6. B. E. Conway, *Ionic hydration in chemistry and biophysics;* Elsevier, Amsterdam, 1981
7. A. R. Cross and C. Anthony, *Biochem. J.,* 192, 421 (1980)
8. B. Z. Zaolavsky, *Aqueous Two-phase partitioning;* Marcel Dekker, New York, 1994
9. P. A. Albertsson, *Partition of cell particles and macromolecules* 3rd ed. Wiley, New York, 1996
10. AmBisomeR, (Developed by NeXstar), www.gileed.com
11. N. T. Parkin, P. Chiu, and R. Coelinph, "Genetically-engineered live attenuated influenza A virus vaccine candidates"; *J. Virol.,* 74, 2772–2778 (1997)
12. E. Sakmann, *Science,* 271, 43–48, (1996)
13. R. J. Lee, L. Huang, Artificial Self-Assembling Systems for Gene Transfer, P. L. Felgner et al. ed., American Chemical Society, Washington D.C., 1996
14. L. Zarif, I. Segarra, T. Jin, D. Hyra, R. J. Mannino; "Amphotericin B cochleates as a novel oral delivery system for the treatment of fungal infections," *26th International Symposium on Controlled Release of Bioactive Materials;* Boston, USA, 1999

What is claimed is:

1. A stable aqueous/aqueous emulsion system, which is prepared with hydrophilic polymers by the method comprising steps of:
    a) selecting appropriate polymeric materials for dispersed phase and continuous phase which are immiscible, biocompatible and have biased partition to the active ingredients to be encapsulated;
    b) selecting appropriate surface modifiers which are charged, non-toxic, and possessing a moderate interfacial tension between the above two phases;
    c) developing phase diagram for the above; and
    d) dispersing the dispersed phase into the continuous phase under an appropriate shear stress.
2. The aqueous/aqueous emulsion system of claim 1 with polymeric surface modifier.
3. An encapsulation comprising the emulsion system of claim 1.
4. The encapsulation of claim 3 which encapsulates protein, peptide, virus, bacterium, or cell.
5. A liposome-based drug formulation which comprises the emulsion system of claim 1.
6. Viral, bacterial or cell microencapsulation comprising the emulsion system of claim 1.
7. A nano-sized preparation comprising the emulsion system of claim 1.
8. The nano-sized preparation of claim 7, wherein the preparation is nano-sized crystallization, nano-sized precipitation or other nano-sized assembly.
9. The stable aqueous/aqueous emulsion system of claim 1, wherein the hydrophilic polymer is dextran, sodium alginate, or polyethylene glycol.

* * * * *